US006998384B2

(12) United States Patent
Floros et al.

(10) Patent No.: US 6,998,384 B2
(45) Date of Patent: Feb. 14, 2006

(54) SURFACTANT PREVENTION OF LUNG COMPLICATIONS FROM CANCER CHEMOTHERAPY

(75) Inventors: Joanna Floros, Hershey, PA (US); David S. Phelps, Hershey, PA (US); Hamid A. Al-Mondhiry, Harrisburg, PA (US); Weixiong Huang, Hershey, PA (US); Guirong Wang, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 253 days.

(21) Appl. No.: 10/317,787

(22) Filed: Dec. 12, 2002

(65) Prior Publication Data

US 2003/0144248 A1    Jul. 31, 2003

Related U.S. Application Data

(60) Provisional application No. 60/339,695, filed on Dec. 12, 2001.

(51) Int. Cl.
*A61K 38/00* (2006.01)
(52) U.S. Cl. ......................................................... 514/8
(58) Field of Classification Search ...................... 514/8
See application file for complete search history.

(56) References Cited

U.S. PATENT DOCUMENTS

| 4,861,756 A |   | 8/1989 | Jackson |
| 5,407,914 A |   | 4/1995 | Cochrane et al. |
| 5,683,982 A |   | 11/1997 | McLean et al. |
| 5,827,825 A |   | 10/1998 | Takei et al. |
| 5,883,084 A | * | 3/1999 | Peterson et al. ............... 514/78 |
| 5,891,844 A |   | 4/1999 | Häfner |
| 5,948,681 A |   | 9/1999 | Scanlin et al. |
| 6,013,619 A |   | 1/2000 | Cochrane et al. |
| 6,436,970 B1 |   | 8/2002 | Häfner et al. |

FOREIGN PATENT DOCUMENTS

| DE | 100 06 179 A1 | 8/2001 |
| EP | 0733 645 A1 | 9/1996 |
| EP | 0383 837 B1 | 2/1998 |
| EP | 0590 006 B1 | 9/2002 |
| JP | 10316587 A2 | 12/1998 |
| WO | WO 95/32992 A1 | 12/1995 |
| WO | WO 01/19392 A1 | 3/2001 |
| WO | WO 01/76619 A1 | 10/2001 |
| WO | WO 01/80633 A2 | 11/2001 |
| WO | WO 02/085308 A2 | 10/2002 |

OTHER PUBLICATIONS

Ito et al. The effects of surfactant-TA on bleomycin-induced lung injury and lung fibroblast proliferation. Nihon Kyobu Shikkan Gakkai Zasshi. Nov. 1997;35(11):1163-72. Japanese.*
Database Medline 'Online! Nov. 1997 Ito M et al: "The effects of surfactant-TA on bleomycin-induced lung injury and lung fibroblast proliferation!" Database accession No. NLM9493441 XP002239521 abstract and Nihon Kyobu Shikkan Gakkai Zasshi. Japan Nov. 1997, vol. 35, No. 11, Nov. 1997, pp. 1163-1172, ISSN; 0301-1542.
Chen et al., Surfactant and corticosteroid effects on lung function in a rat model of acute lung injury, Crit Care Med Nov. 2001; 29(11):2169-75 (Abstract).
Hohlfield et al., The role of pulmonary surfactant in obstructive airways disease, Eur Respir J Feb. 1997; 10(2):482-91 (Abstract).
Otsubo et al., Characterization of synthetic lung surfactant activity against proinflammatory cytokines in human monocytes, Biol Pharm Bull Mar. 2002; 25(3):312-7 (Abstract).
Wu et al., Effect of surfactant on pulmonary expression of type IIA PLA(2) in an animal model of acute lung injury, Am J Physiol Lung Cell Mol Physiol Apr. 2002; 282(4);L743-50 (Abstract).
Huang et al., Combined SP-A-bleomycin effect on cytokines by THP-1 cells: impact of surfactant lipids on this effect, Am J Physiol Lung Cell Mol Physiol 283:L94-L102, 2002.

* cited by examiner

*Primary Examiner*—Christopher R. Tate
*Assistant Examiner*—Maury Audet
(74) *Attorney, Agent, or Firm*—McKee, Voorhees & Sease, P.L.C.

(57) ABSTRACT

A means and method for treating pulmonary fibrosis in animals is described. The compositions include surfactant lipids in a pharmaceutically acceptable carrier. Surfactant lipids have been found to suppress the synergistic effect of bleomycin and SP-A in enhancing proinflammatory cytokine production. Surfactant lipids are also effective in the prevention and treatment of pulmonary fibrosis resulting from exposure to inflammatory agents affecting cytokine production.

6 Claims, 7 Drawing Sheets

SURFACTANT PREVENTION OF LUNG COMPLICATIONS FROM CANCER CHEMOTHERAPY

PRIORITY CLAIM

This application claims priority to U.S. Provisional Application Ser. No. 60/339,695 filed Dec. 12, 2001.

FIELD OF THE INVENTION

This invention relates to the use of surfactant lipids for a variety of therapeutic uses, including the treatment of pulmonary inflammation and fibrosis.

BACKGROUND OF THE INVENTION

Pulmonary fibrosis (PF) is a complicated, chronic illness characterized by abnormal formation of fiberlike scar tissue in the lungs. Most patients with PF first have alveolitis, or inflammation of the lung, which drives the scarring process. If the disease progresses, the lungs eventually thicken and become stiff, which prevents oxygen from getting from the air sacs into nearby blood vessels that deliver oxygen to the body, thus making it more difficult for the person to breathe.

PF affects each person differently, and progresses at varying rates. Generally, the patient's breathlessness becomes worse over time, and daily activities such as walking, climbing stairs, etc. become more difficult. As the disease advances, the patient may require supplemental oxygen to meet the demands of the body. PF causes hypoxemia, or a lack of oxygen in the blood. This condition may lead to high blood pressure in the lungs (pulmonary hypertension) and put a strain on the heart that can lead to heart dysfunction. PF has also been associated with heart attack, respiratory failure, stroke, pulmonary embolism, and lung infection. In some cases PF can even be fatal.

There are many known causes of PF, including occupational and environmental exposures, sarcoidosis, medications, radiation, connective tissue or collagen diseases such as rheumatoid arthritis and systemic sclerosis, and genetic/familial causes (less common). When all known causes of PF have been excluded, the condition is labeled as idiopathic pulmonary fibrosis (IPF). No matter what the cause, in each case of PF the lung is reacting to some insult by developing inflammation which leads to an exaggerated or uncontrolled healing response that, over time, produces fibrous scar tissue. The histological features of pulmonary fibrosis in human and animal studies include inflammatory cell recruitment, fibroblast proliferation and collagen synthesis. A number of studies concerning the pathogenesis of pulmonary fibrosis have focused on the role of inflammatory cells, especially alveolar macrophages, in the fibrotic process.

Current treatments for PF focus on improving symptoms and slowing progression of the disease. These include administration of corticosteroids to reduce inflammation, which are often used in combination with a drug to suppress the body's immune response, such as azathioprine or cyclophosphamide. Unfortunately, this treatment approach improves symptoms and/or improves the life span only some of the time. These drugs can also cause numerous side effects, some of which are severe. Interferon gamma-Ib is a new drug shown to be superior to corticosteroids in preliminary studies. However, its current cost (approximately $100,000/year) is prohibitive for most patients.

In advanced cases of PF, doctors may consider lung transplantation. This procedure is most often performed in patients under 60 years of age whose PF has been unresponsive to other treatments. However, lung transplantation is extremely invasive and expensive, and often requires patients to wait months to years until matching organs become available. Further, many patients are ineligible for transplantation.

There is therefore a need in the art for a new method and means of treating PF that overcomes at least some of the disadvantages associated with current treatments.

As noted above, certain medications are associated with the development of pulmonary fibrosis, including nitrofurantoin, amiodarone, and the chemotherapeutic agents bleomycin, cyclophosphamide, and methotrexate. Bleomycin is a group of glycopeptides isolated from *Streptomyces verticillus*. Although it is an effective antineoplastic agent, bleomycin-induced pulmonary fibrosis can become fatal and therefore limits the usefulness of the drug. Bleomycin has a differential effect on pulmonary fibrosis. Evidence suggests that there is an individual susceptibility in pulmonary fibrosis, and genetic factors are implicated in the pathogenesis of fibrosis to explain variation in susceptibility. Bleomycin induces inflammatory cells from human and animal lung to secrete multifunctional cytokines, such as TNF-$\alpha$, IL-$\beta$, IL-8, and TGF-$\beta$.

The mechanism of bleomycin-induced cytokine production is not well understood. The cytotoxic effect of bleomycin is believed to be related to DNA damage that is characterized by the appearance of DNA damage-inducible proteins and apoptosis. There is also increased activity of NF-kB, which may result from the increase of reactive oxygen species by bleomycin. NF-kB is a transcriptional factor that regulates the expression of many cytokine genes. Among these, TGF-$\beta$ is considered to be an important cytokine related to fibroblast proliferation and collagen synthesis and TNF-$\alpha$ is considered to be a central mediator in bleomycin-induced pulmonary fibrosis. TNF-$\alpha$ receptor knockout mice have been shown to be protected from pulmonary injury following exposure to bleomycin.

Pulmonary surfactant is essential for normal lung function. The primary function of pulmonary surfactant is to reduce surface tension at the air-liquid interface of the alveolus, which in turn prevents lung collapse at low lung volumes.

Surfactant protein A (SP-A), in addition to surfactant-related function, plays a role in local host defense and regulation of inflammatory processes in the lung. Moreover, SP-A regulates cytokine expression by alveolar macrophages (i.e. IL-1, TNF-$\alpha$ etc.) and expression of SP-A itself is regulated by cytokines (such as IFN-$\gamma$). SP-A also stimulates fibroblasts to produce collagen, and may affect cytokine expression by lung fibroblasts.

SP-A is a collagenous C-type lectin or collectin and its carbohydrate recognition domain (CRD) is involved in binding SP-A to pathogens and promoting phagocytosis of these pathogens by the macrophages. In the macrophage-like THP-1 cell line, human SP-A stimulates production of TNF-$\alpha$, IL-$1\beta$, IL-8, and IL-6 in a dose- and a time-dependent manner. SP-A-enhanced TNF-$\alpha$ production appears to involve NF-kB activation. SP-A also enhances immune cell proliferation and increases expression of some cell surface proteins. In addition, SP-A knockout mice show an increased susceptibility to infection. A recent in vivo study suggests a role for SP-A in neutrophil recruitment into the lungs of preterm lambs.

Surfactant lipids (surfactant TA, Survanta; Infasurf; Curosurf; et al.) can modulate adherence and superoxide production of neutrophils. Surfactant lipids inhibit several SP-A regulated immune cell functions, including stimulation of macrophages. Surfactant lipids and SP-A may be counter-regulatory and changes in the relative amounts of surfactant lipids to SP-A may be important in determining the immune status of the lung. Although most of SP-A in the normal alveolar space is thought to be lipid-associated, "lipid-free" SP-A could increase if the balance between SP-A and surfactant lipid was altered under certain conditions.

The present inventors have now found that SP-A plays a role in bleomycin-induced fibrosis, by affecting cytokine expression and/or collagen production. It has further been discovered that "lipid-free" SP-A, the result of an imbalance of SP-A and surfactant lipids following bleomycin treatment, may enhance the effect of bleomycin on proinflammatory cytokine production, and may be partly responsible for bleomycin-induced pulmonary fibrosis. Based on these findings, the present inventors have now determined that the administration of surfactant lipids is effective in suppressing the pulmonary inflammatory processes induced by bleomycin or other causative agents, thereby preventing PF.

It is therefore a primary objective of the present invention to provide a means of preventing and/or treating pulmonary fibrosis.

It is another objective of the present invention to provide a means of preventing and/or treating bleomycin-induced pulmonary fibrosis.

It is a further objective of the present invention to provide a means of preventing and/or treating pulmonary fibrosis through the administration of surfactant lipids.

It is still a further objective of the present invention to provide a means of preventing and/or treating pulmonary fibrosis that is more effective than previously available treatments for PF.

It is a yet a further objective of the present invention to provide a means of preventing and/or treating pulmonary fibrosis that has a lesser degree of side effects than previously available treatments for PF.

These and other objectives will become clear from the foregoing detailed description.

SUMMARY OF THE INVENTION

The present invention is directed to a method and means for preventing and treating pulmonary fibrosis (PF) through the administration of surfactant lipids. The invention is based on the finding that both SP-A and bleomycin stimulate production of inflammatory cytokines, and that there is a synergistic effect when both agents are used. The significantly elevated cytokine levels resulting from this synergism appear responsible for pulmonary fibrosis. It has surprisingly been found that administration of surfactant lipids significantly suppress the synergistic effect of SP-A/inflammatory agents on cytokine production. This finding may in turn be used in the prevention and treatment of pulmonary complications observed during chemotherapy, as well as in general prevention and treatment of PF.

BRIEF DESCRIPTION OF THE DRAWINGS

FIG. 1 illustrates dose-response cytokine production after bleomycin treatment by THP-1 cells. Differentiated THP-1 cells were stimulated with the indicated concentration of bleomycin for 4 h or 6 h. TNF-α (Panel A) and IL-8 (Panel B) levels in culture medium at 4 h incubation and IL-1β (Panel C) at 6 h were quantified by ELISA. The effect of Ara-C on TNF-α was examined at 4 h (panel D). Data are derived from 5 separate experiments except the Ara-C experiments which are from two experiments in triplicate. Results are given as means±SEM. The indicated values (*) are significantly different (p<0.05) from points obtained in the absence of bleomycin.

FIG. 3 illustrates the combined effect of SP-A and bleomycin on cytokine production by THP-1 cells. Differentiated THP-1 cells were stimulated with SP-A (10 μg/ml) and bleomycin (BLM 5, 50 mU/ml) simultaneously for 4 h or 6 h. TNF-α (Panel A) and IL-8 (Panel B) in culture medium at 4 h incubation and IL-1β (Panel C) at 6 h were quantified. Data are derived from 5 separate experiments, and the results are given as means±SEM. The indicated values (*) are significantly different (p<0.05) from points with SP-A alone and points with the same dose of bleomycin but without SP-A.

FIG. 4 illustrates the combined effect of bleomycin and SP-A on cytokine mRNA levels. Differentiated THP-1 cells were stimulated with SP-A (10 μg/ml) and/or bleomycin (BLM 5 mU/ml) simultaneously. After a 2 h (Panel A) or a 4 h (Panel B) incubation, the cells were processed for quantification of cytokine mRNA by RNAse protection assay (RPA). The mRNA level for TNF-α, IL-1β, and IL-8 in 2 μg of total cell RNA was normalized to mRNA for ribosomal protein L32. Data shown in Panel A and B were derived from 4 and 3 separate experiments, respectively. Results were given as means±SEM. The indicated values are significantly different (p<0.05) from points treated with SP-A (*) and bleomycin (^) alone, respectively. LPS (0.1 ng/ml) treatment was included as a positive control.

FIG. 5 illustrates the effect of preincubation of SP-A and bleomycin (BLM) on TNF-α production. Differentiated THP-1 cells were stimulated with SP-A (10 μg/ml) and bleomycin (50 mU/ml) that were either preincubated together for 15 min at 37° C. before adding them to the cells, or were not preincubated. Data are derived from 4 separate experiments. Results were given as means±SEM. The indicated values (*) are significantly different from points without preincubation.

FIG. 6 illustrates the effect of surfactant lipids (Infasurf) on SP-A and bleomycin induced TNF-α production. Infasurf at indicated concentration was preincubated separately with SP-A (10 μg/ml), bleomycin (5 mU/ml), and SP-A+bleomycin for 15 min at 37° C. before addition to THP-1 cells. Incubation was continued for 4 h. Cells were incubated for 4 h after treatment. Culture medium was then collected and TNF-α level was quantified by ELISA. Data shown are from single experiment in triplicate, but are representative of three experiments. Results are given as means±SEM. The indicated values (*) are significantly different (p<0.05) from points obtained in the absence of Infasurf.

DETAILED DESCRIPTION OF THE INVENTION

The present invention relates to the discovery that SP-A plays a role in bleomycin-induced fibrosis by affecting cytokine expression and/or collagen production. The invention is premised on the finding that surfactant lipids significantly suppress the additive or synergistic effect on cytokine production observed in the presence of both SP-A and bleomycin, or other causative factors associated with lung inflammation and fibrosis.

It should be understood that while the invention is specifically described in terms of pulmonary inflammation and fibrosis as a result of treatment with bleomycin, the invention is also effective in treating pulmonary inflammation and fibrosis resulting from other lung inflammatory agents. These agents include, but are not limited to nitrofurantoin, amiodarone, cyclophosphamide, and methotrexate, as well as other known and unknown causes.

While not wishing to be bound by any theory, it is believed that treatment with bleomycin or exposure to other inflammatory agents causes a substantive change in the patient's lung surfactant, which in turn enhances the stimulatory influence of SP-A. Under normal physiological conditions, most of the SP-A in the alveoli is combined with surfactant lipids in the form of a surfactant lipoprotein complex. It appears that these SP-A/lipid complexes do not affect cytokine production, perhaps because the complexed SP-A is unable to interact directly with immune cells. Therefore, it is possible that if the lipids are reduced in quantity or quality, the stimulatory influence of SP-A is enhanced. In fact, results in animal models have demonstrated that bleomycin-induced pulmonary fibrosis causes changes in surfactant composition and function. Studies in rats indicate there is a significant increase in SP-A but not of surfactant phospholipids in response to bleomycin. It has also been shown that although surfactant lipids by themselves have no effect on cytokine production, surfactant lipids completely inhibit SP-A proinflammatory function observed in both, ELISA and RPA assays of cytokine proten and mRNA, respectively. Thus, surfactant lipids can significantly inhibit the combined effects of SP-A and inflammatory agents on cytokines.

The human SP-A locus is located on the large arm of chromosome 10 and consists of two functional genes and one pseudogene. The order for the SP-A sequences from the centromere to the telomere is as follows: SP-A2, pseudogene, and SP-A1. The transcriptional orientation of the SP-A2 and pseudogene is opposite to that of SP-A1. As discussed above, SP-A plays a role in bleomycin induced fibrosis, by affecting cytokine expression and/or collagen production. Functional differences exist among the various SP-A alleles with regard to their ability to induce cytokine expression and/or collagen production by alveolar macrophages and/or lung fibroblasts. These differences may explain in part the individual variability observed in the susceptibility of fibrosis among individuals.

Although the mechanism of action of SP-A in cytokine production is not known, it is likely that it involves interaction with a cell membrane molecule, possibly the C1q receptor, activating intracellular events including the eventual activation of NF-kB. When SP-A and bleomycin are added to the cell at the same time, the levels of both TNF-α and IL-8 have been found to be higher than the sum of each cytokine induced by SP-A or bleomycin alone. Analysis of mRNA shows that the combined treatment of SP-A and bleomycin exhibits an additive effect on the expression of TNF-α, IL-1β, and IL-8 mRNA. Although bleomycin itself does not induce a significant increase of IL-1β mRNA, it greatly enhances the level of IL-1β mRNA after being combined with SP-A. The fact that the combined effect of SP-A+bleomycin shown in cytokine protein production is much greater than that observed in mRNA level indicates that various post-transcriptional and post-translational mechanisms may be involved in bleomycin-induced proinflammatory cytokine production by THP-1 cells in response to SP-A.

As used herein, the terms "surfactant lipids" or "surfactant TA" or "Infasurf" or "Survanta" are defined as natural or artificial substances composed of phospholipids, neutral lipids, and hydrophobic surfactant-associated proteins B and C (SP-B and SP-C) capable of forming a layer between the alveolar surface and the alveolar gas and reducing alveolar collapse by decreasing surface tension within the alveoli. Current commercially available surfactant lipids are derived from human, animal (bovine), or synthetic sources, and may be purchased under the trade names Infasurf® (calfactant), Exosurf® (surfactant, synthetic), and Survanta® (beractant). However, persons skilled in the art can readily appreciate that various other brands and types of surfactant from various sources that may become available in the future are also appropriate for use in this invention.

The surfactant lipids of the present invention may be generally used for the prophylaxis and treatment of pulmonary fibrosis. The surfactant lipids are administered along with a pharmaceutically acceptable carrier. Any pharmaceutically acceptable carrier may be generally used for this purpose, provided that the carrier does not significantly interfere with the stability or bioavailability of the surfactant lipid compounds of this invention. Examples of such carriers and methods of formulating such carrier may be found in Remington's Pharmaceutical Sciences.

The surfactant lipids of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells. Although to date surfactant lipids are conventionally administered intratracheally, persons skilled in the art can readily appreciate that other forms of administration may be suitable as well.

In addition to the active compounds i.e. the surfactant lipids, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally, intratracheally, intranasally, or orally, and compositions which can be administered buccally or sublingually.

The pharmaceutical preparations of the present invention are manufactured in a manner which is itself well known in the art. For example the pharmaceutical preparations may be made by means of conventional mixing, granulating, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, crosslinked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral or intratracheal administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The surfactant lipid compositions of the present invention are administered along with a pharmaceutically acceptable carrier in an amount sufficient to prevent pulmonary fibrosis and/or treat an active case of the disease. The surfactant lipid compounds of this invention have extremely low toxicity and a low degree of side effects even at high doses. The dosing range of the surfactant lipid compositions will vary depending on a number of factors, such as whether it is used for prophylaxis or treatment of active disease, route of administration, dosing schedule, etc.

As a general guideline, the therapeutic dose of surfactant lipids may range between about 30–800 mg/kg. However, persons skilled in the art can readily appreciate that lower or higher doses of surfactant may be appropriate depending on a number of factors, including cost, severity of the disease, etc. The foregoing doses may be administered as a single dose or may be divided into multiple doses for administration. The surfactant lipid compositions may be administered once to several times daily. For prevention of PF, a typical dosing schedule could be, for example, 30–800 mg/kg weekly beginning 1–2 weeks prior to exposure to a pulmonary inflammatory agent, such as bleomycin, until 1–2 weeks post-exposure.

The following examples are offered to illustrate but not limit the invention. Thus, it is presented with the understanding that various formulation modifications as well as method of delivery modifications may be made and still are within the spirit of the invention.

EXAMPLE 1

Effects of SP-A on Bleomycin-Induced Cytokine Production and mRNA Expression in THP-1 Cells Materials and Methods Cell Culture The THP-1 cell line was obtained from the American Type Culture Collection. Cells were grown in RPMI 1640 medium (Sigma) with 0.05 mM 2-mercaptoethanol containing 10% fetal calf serum (FCS; Summit Biotechnology) at 37° C. in an atmosphere of 5% $CO_2$. The cells were split periodically and used at passages 8–15 in the various experiments. After differentiation with $10^{-8}$ M Vitamin $D_3$ for 72 h, cells were pelleted and washed with cold PBS. The cell pellet was then resuspended in complete RPMI 1640 medium with 10% FCS at a density of $2 \times 10^6$ cells/ml in 24-well culture plates, and exposed to bleomycin and SP-A. Cell viability was determined by trypan blue exclusion. Under the conditions employed in this study, neither bleomycin nor SP-A appeared to have any effect on the viability of THP-1 cells. Incubations were terminated by pelleting the cells. Supernatants and/or cell pellet were stored at −80° C. until assayed.

Bleomycin and Native Human SP-A

Bleomycin (Blenoxane; Bristol-Myers Squibb Co) solutions were prepared immediately before use with endotoxin-free saline (American Pharmaceutical Partners, Inc.).

Lipopolysaccharide (LPS) was not detected in the stock solution of bleomycin at a bleomycin concentration of 5 U/ml (IU=1 mg) using the method described below.

SP-A was purified from bronchoalveolar lavage of alveolar proteinosis patients with 1-butanol extraction. After extraction of whole surfactant with butanol, the pellet was completely dried with a flux of nitrogen gas and then homogenized twice in a freshly prepared buffer (20 mM n-Octyl β-D-Glucopyranoside, 10 mM HEPES, 150 mM NaCl, pH 7.4). After pelleting, the insoluble protein was dissolved in 5 mM Tris-HCl, pH 7.5 and dialyzed for 48 h against the same buffer. The dialyzed solution was centrifuged (210K×g, 4° C., 30 min) and the supernatant containing SP-A was collected and stored at −80° C. The purified protein was examined by two-dimensional gel electrophoresis followed by western blotting and silver staining, and was found to be greater than 98% pure. Protein concentration was determined with the micro bicinchoninic acid method (Pierce) with RNAse A as a standard. SP-A was stored at −80° C. Endotoxin content was determined with the QCL-1000 Limulus amebocyte lysate assay (Biowhittaker). This test indicated that the SP-A used contained <0.1 pg LPS/10 µg SP-A.

Stimulation of THP-1 Cells with SP-A and Bleomycin

After differentiation with $10^{-8}$ M of vitamin $D_3$ for 72 h, THP-1 cells were pelleted and washed as described above. Cells at a density of $2\times10^6$ cells/ml were incubated at 24 well culture plates. For dose-response study, cells were stimulated with bleomycin at concentrations ranging from 0–100 mU/ml. Time-dependent secretion of cytokines following bleomycin treatment was studied from 0–24 h with 5 and 50 mU/ml of bleomycin. In experiments where the combined effects of SP-A and bleomycin were examined, SP-A (10 µg/ml) and bleomycin (5 or 50 mU/ml) were added to cells simultaneously, unless otherwise noted. After treatment, the culture medium was collected at 4 h or 6 h for the ELISA assay of cytokine production and cells were harvested at 2 h or 4 h for cytokine mRNA analysis.

Cytosine arabinoside (Ara-C, Cytosar-U, Pharmacia & Upjohn) was included in some experiments to confirm the specificity of the effect of bleomycin on proinflammatory cytokine production by THP-1 cells. Ara-C is another antineoplastic agent with known cytotoxicity. Although it has not been associated with pulmonary fibrosis and cytokine production, it has been shown to cause non-cardiogenic pulmonary edema. Ara-C, at concentrations ranging from 0.1 to 5 mM in culture medium, was used for evaluating the effect of Ara-C on TNF-α. The conditions employed in the Ara-C experiments were the same as those in bleomycin studies except that only a 4 h time point was done.

Infasurf Inhibition of Cytokine Production

Infasurf (Forest Pharmaceuticals), an extract of natural surfactant from calf lung, was used as a source of surfactant lipid. Infasurf was supplied by the manufacturer as a suspension containing 35 mg phospholipids/ml of sterile saline. Infasurf is predominately phosphatidylcholine and contains ~2% wt/wt ptoetin that includes SP-B and SP-C, but no SP-A. Infasurf in concentrations ranging from 100 to 800 µg/ml was used in the experiments for ELISA assay of cytokine production, but only a single dose (400 µg/ml) of Infasurf was used in the experiment for mRNA analysis. Infasurf was preincubated separately with SP-A (10 µg/ml), bleomycin (5 mU/ml), and SP-A+bleomycin for 15 min at 37° C. before addition to the THP-1 cells. Cells were incubated for 4 h after the treatment. Culture medium and cell pellets were then collected for ELISA assay and mRNA analysis, respectively.

ELISA Assay

The ELISA assays for TNF-α, IL-8, and IL-1β (OptEIA Human ELISA Sets, Pharmingen) were performed according to the instructions recommended by the manufacturer. The ELISA kits were capable of measuring levels of 7.8–500 pg/ml for TNF-α, 6.2–400 pg/ml for IL-8 and 20–1000 pg/ml for IL-1β. A reference curve for each of these cytokines was obtained by plotting the concentration of several dilutions of standard protein versus the corresponding absorbance.

Analysis of Cytokine mRNA

Total RNA was isolated from THP-1 cells at 2 h or 4 h after treatment by using Rneasy Mini Kits (QIAGEN) according to the protocol of the RNeasy Mini Handbook. Cytokine mRNA quantification was performed by ribonuclease protection assay (RPA). RiboQuant™ Ribonuclease RPA Starter Package and a Customized Human Template Set (Pharmingen) were used to analyze TNF-α, IL-1β, and IL-8 mRNA in one assay. The customized template set contains DNA templates that can be used for T7 RNA polymerase-directed synthesis of $\alpha$-$^{32}$P-UTP-labeled, anti-sense RNA probes. These can be hybridized to TNF-α, IL-1β, and IL-8 mRNA. Templates for the L32 and Statistics Values are presented as means±SEM. Data were analyzed using SigmaStat statistical software. For each experiment, statistical treatment included a one-way analysis of variance (ANOVA) followed by a Student-Newman-Keuls test for pairwise comparison and was judged to be significantly different at $p<0.05$.

Results

Dose-Response and Time Course Studies of Bleomycin Effects on Stimulation of Cytokine Production by THP-1 Cells To study the response of THP-1 cells to bleomycin stimulation, a dose-response and a time course of bleomycin effects on TNF-α, IL-1β, and IL-8 levels was performed. The concentrations of bleomycin for the dose-response study ranged from 0–100 mU/ml, which spans a relevant pharmacological dose. As shown in FIG. 1, a bleomycin concentration as low as 0.5 mU/ml increased both TNF-α and IL-8 levels (panels A and B), but a higher concentration of bleomycin (50 mU/ml) was needed to increase the IL-1β level significantly (panel C). Cytokine production continued to increase as the bleomycin dose was increased to 100 mU/ml. In contrast, the TNF-α even after Ara-C treatment did not differ from that of control (panel D).

Figure 1A:
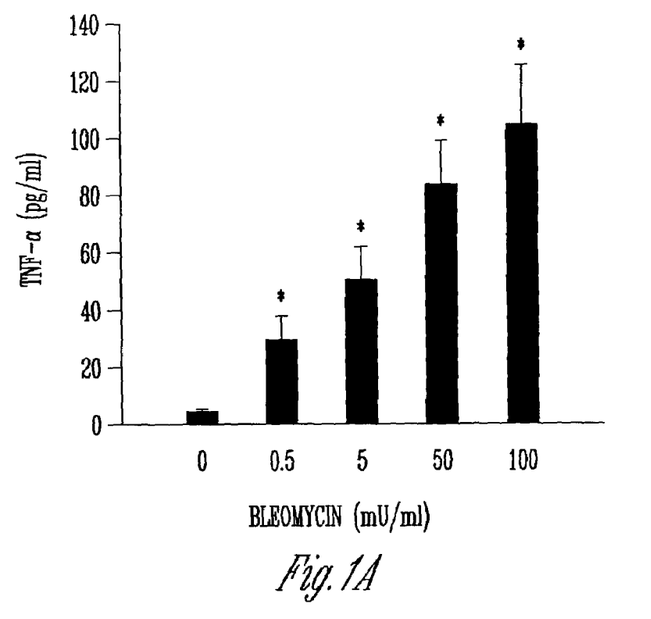
Figure 1B:
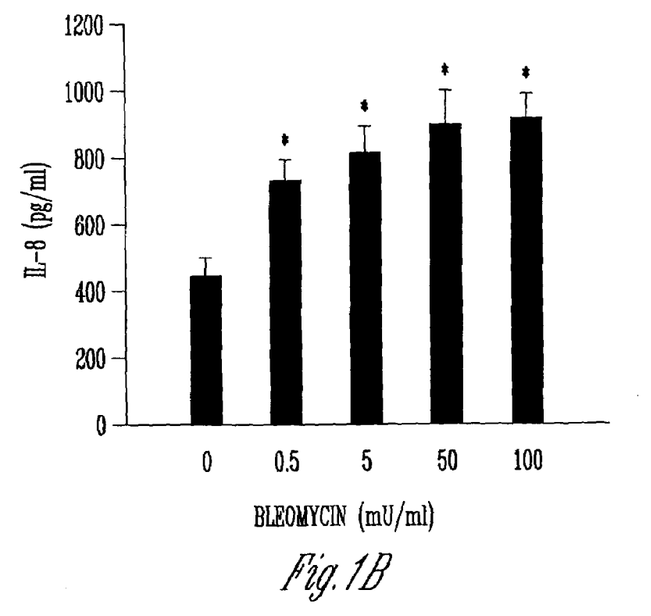
Figure 1C:
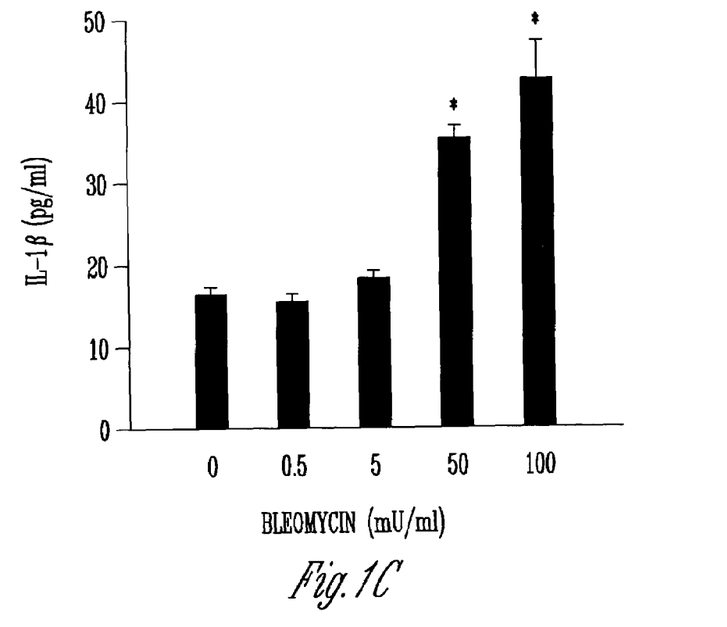
Figure 1D:
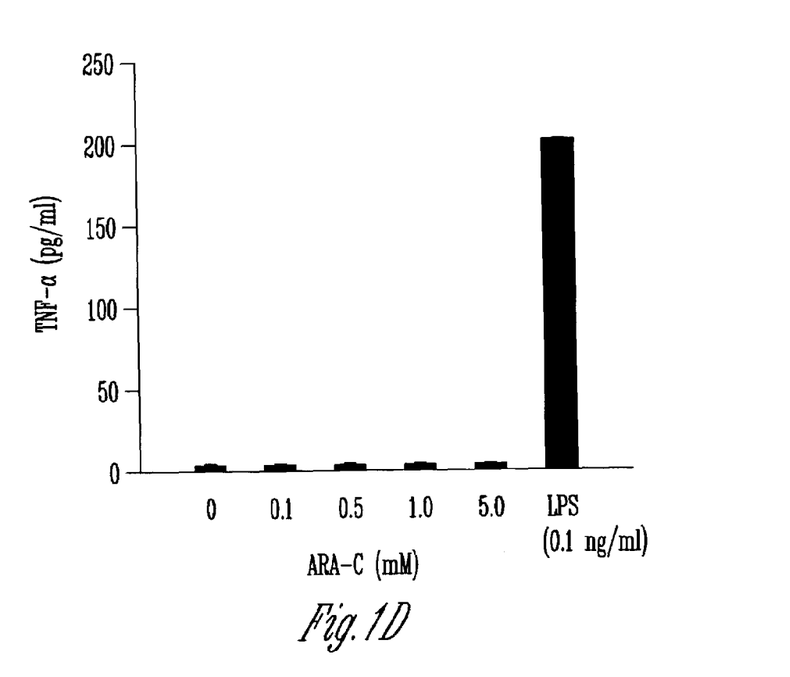
Figure 2A:
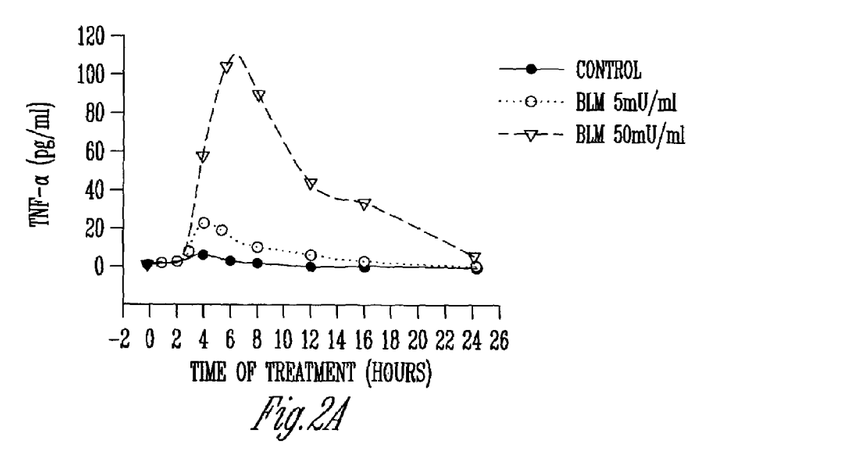
FIG. 2 illustrates the time course of cytokine production after bleomycin treatment. Differentiated THP-1 cells were incubated in the presence of 0, 5, 50 mU/ml bleomycin for the indicated time. TNF-α (Panel A), IL-8 (Panel B) and IL-1β (Panel C) levels in culture medium were quanitifed by ELISA.
Figure 2B:
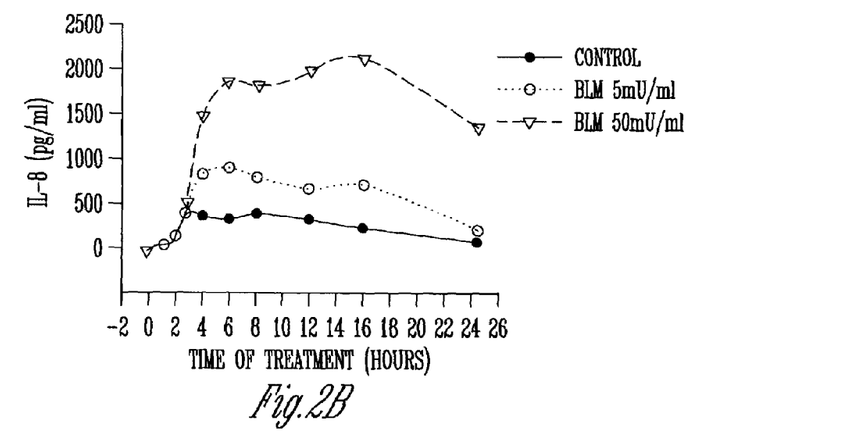
Figure 2C:
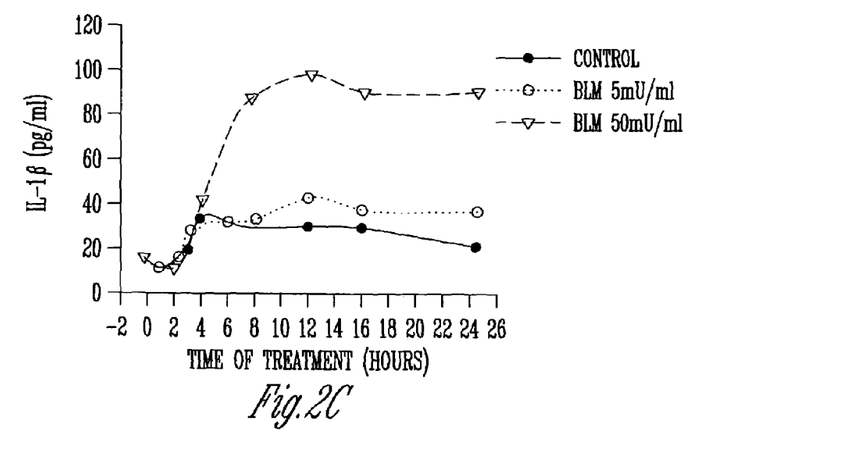

FIG. 2 illustrates the time-dependent secretion (0–24 h) of TNF-α, IL-1β, and IL-8 by THP-1 cells in the presence or absence of different bleomycin doses. The basal level of TNF-α at 0h (starting point) was low. The increase of TNF-α levels was usually detected at 3 h following bleomycin treatment and quickly reached a maximum by 4 to 6 h depending on the dose selected (FIG. 2A). The content of TNF-α subsequently decreased and returned to background levels at 24 h. Initially, IL-8 had a similar response pattern to TNF-α, with respect to its increase and peak response time, but after reaching maximal level at around 5 h, IL-8 didn't show a significant decline until 24 h (FIG. 2B). The level of IL-1β increased much later (FIG. 2C) than that of TNF-α and IL-8, and reached a peak at 10 h after bleomycin treatment. Unlike that of TNF-α and IL-8, the level of IL-1β then did not decline, but remained elevated over the 24 h test period.

Figure 3A:
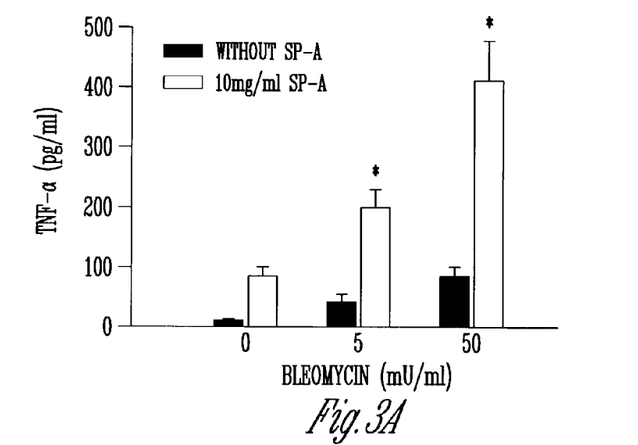
Figure 3B:
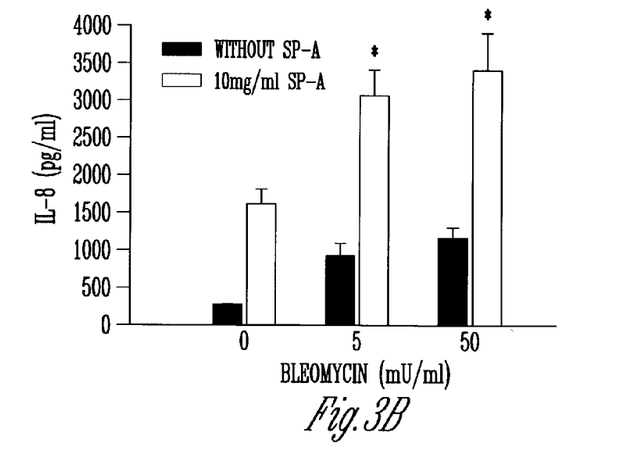
Figure 3C:
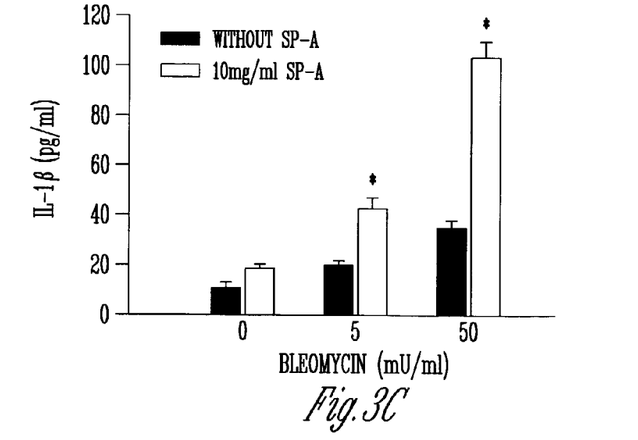

The Combined Effect of SP-A and Bleomycin on Cytokine Production and mRNA Expression by THP-1 Cells After testing the effects of bleomycin treatment on TNF-α, IL-1β, and IL-8 production by THP-1 cells, the combined effects of SP-A and bleomycin on cytokine production was examined. A dose of 10 μg/ml of SP-A was chosen rather than the dose of 50 μg/ml used in previous experiments, as the low dose may better identify synergistic or additive effects of the two substances. As shown in FIG. 3A, TNF-α values induced by SP-A (10 μg/ml) alone and bleomycin (5 mU/ml) alone were 86.6±11.5 pg/ml and 45.9±10.6 pg/ml, respectively. But the combined treatment increased the level to 201.7±34.3 pg/ml. High concentration of bleomycin (50 mU/ml) alone induced a TNF-α level of 82.1±17.3 pg/ml, while the value of the combined effect was 416±61.9 pg/ml. There was a similar response pattern for IL-8 when the combined effects of SP-A and bleomycin were examined (FIG. 3B). Because IL-1β reached a maximum value at a later time point than TNF-α and IL-8 did, we measured its level at 6 h after treatment. The means of IL-1β levels (FIG. 3C) induced by the combined treatment were greater than the sum of the separate means by SP-A or bleomycin alone as seen with TNF-α and IL-8. SP-A and bleomycin appear to have synergistic effects on TNF-α, IL-1β, and IL-8 production by THP-1 cells.

Figure 4A:
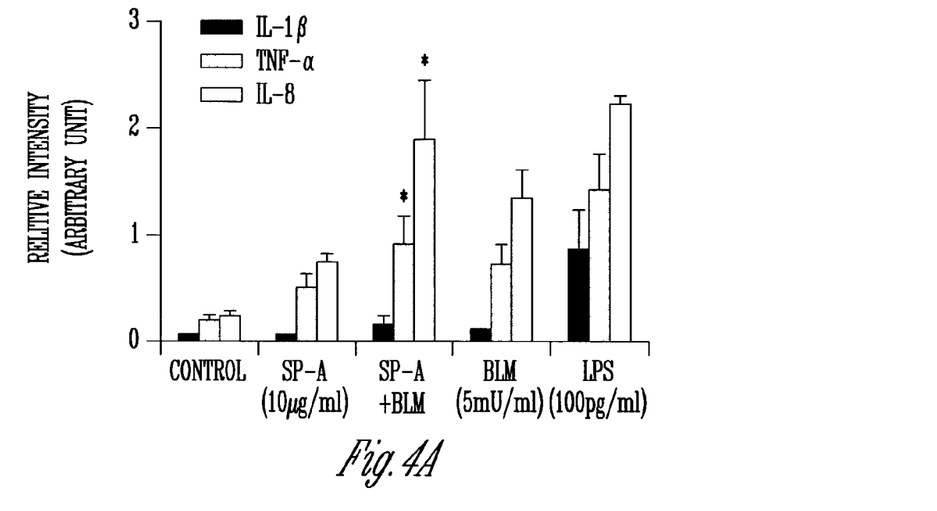
Figure 4B:
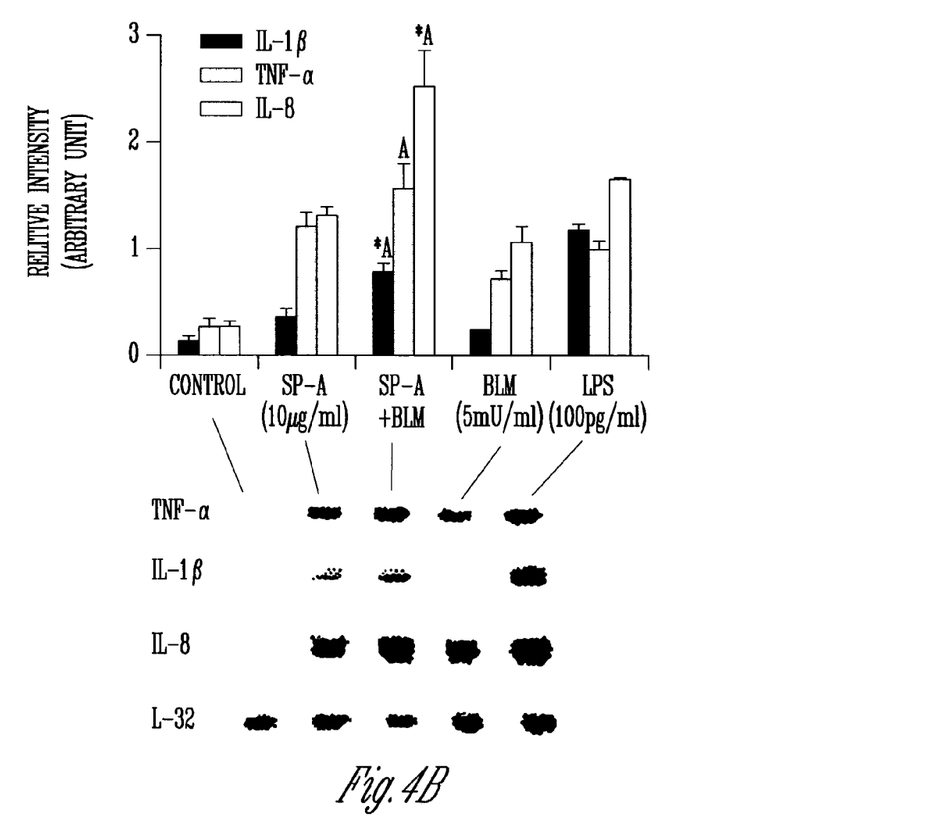

The mRNA levels of TNF-α, IL-1β, and IL-8 were measured by RPA. THP-1 cells were treated with SP-A (10 μg/ml) and/or bleomycin (5 mU/ml) for 2 h and 4 h separately. LPS-treated groups (0.1 ng/ml) were included as a positive control. After 2 h of incubation (FIG. 4A), TNF-α and IL-8 mRNA significantly increased as compared to the control ($p<0.05$). When the cells were treated with SP-A+bleomycin, the relative intensity of TNF-α mRNA increased from 0.51±0.27 (SP-A alone) to 0.95±0.21 ($p<0.05$), but no significant difference was observed between SP-A+bleomycin and bleomycin alone (0.95±0.21 vs. 0.74±0.20). A similar response pattern was also seen with IL-8 mRNA. Very low levels of IL-1β mRNA were detected in all SP-A- and bleomycin-treated cells, but LPS significantly increased the level of IL-1β mRNA at 2 h. The effect of SP-A and bleomycin on IL-1β mRNA expression at 4 h were greater than that at 2 h. A significant increase of IL-1β mRNA expression was observed when SP-A treatment was combined with bleomycin compared to bleomycin alone (FIG. 4B). The IL-8 mRNA level (2.47±0.75) following SP-A+bleomycin treatment was significantly higher ($p<0.05$) than that with SP-A alone (1.26±0.14) or bleomycin alone (1.02±0.16). For TNF-α the differences at 4 h did not reach statistical significance. These results together indicate an additive effect of SP-A and bleomycin on the TNF-α, IL-1β, and IL-8 mRNA expression.

Figure 5:
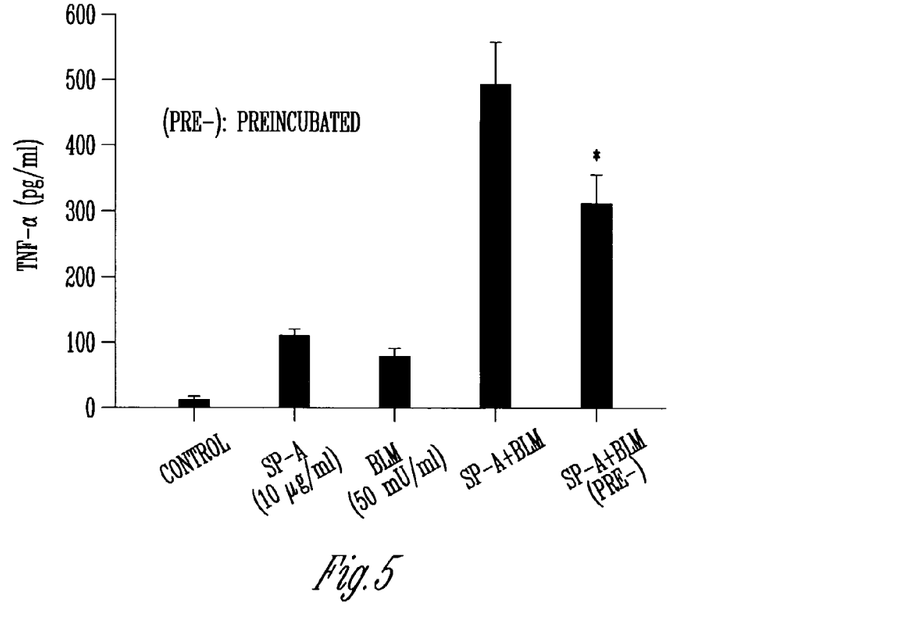

When SP-A (10 μg/ml) was preincubated with bleomycin (50 mU/ml) 15 min before addition to the cells, the TNF-α level was significantly lower than that without preincubation (FIG. 5). However, the synergistic effects on TNF-α production remained. There was a similar response with respect to IL-8 production.

Figure 6:
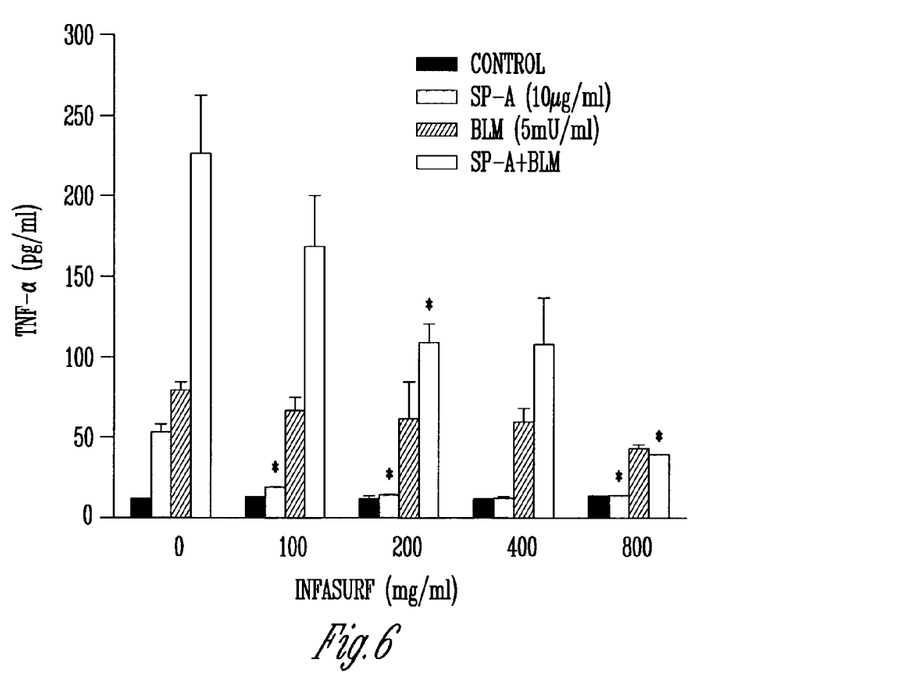

The Inhibitory Effect of Infasurf on SP-A and Bleomycin-Induced Cytokine Production and mRNA Expression The ability of surfactant lipids to modulate cytokine level was examined. As shown in FIG. 6, Infasurf had no effect on TNF-α level in the absence of SPA and bleomycin. SP-A-induced TNF-α level was significantly reduced by Infasurf at 100 μg/ml and was totally inhibited with a higher dose of Infasurf.

In contrast, the bleomycin effect was not significantly reduced by Infasurf even at 800 μg/ml. Infasurf decreased the TNF-α level induced by SP-A+bleomycin in a dose-dependent pattern. The TNF-α level was significantly decreased from 226.8±35.7 pg/ml in the absence of Infasurf to 109±19.3 pg/ml and 41.5±0.7 pg/ml at 200 μg/ml and 800 μg/ml of Infasurf, respectively.

Figure 7:
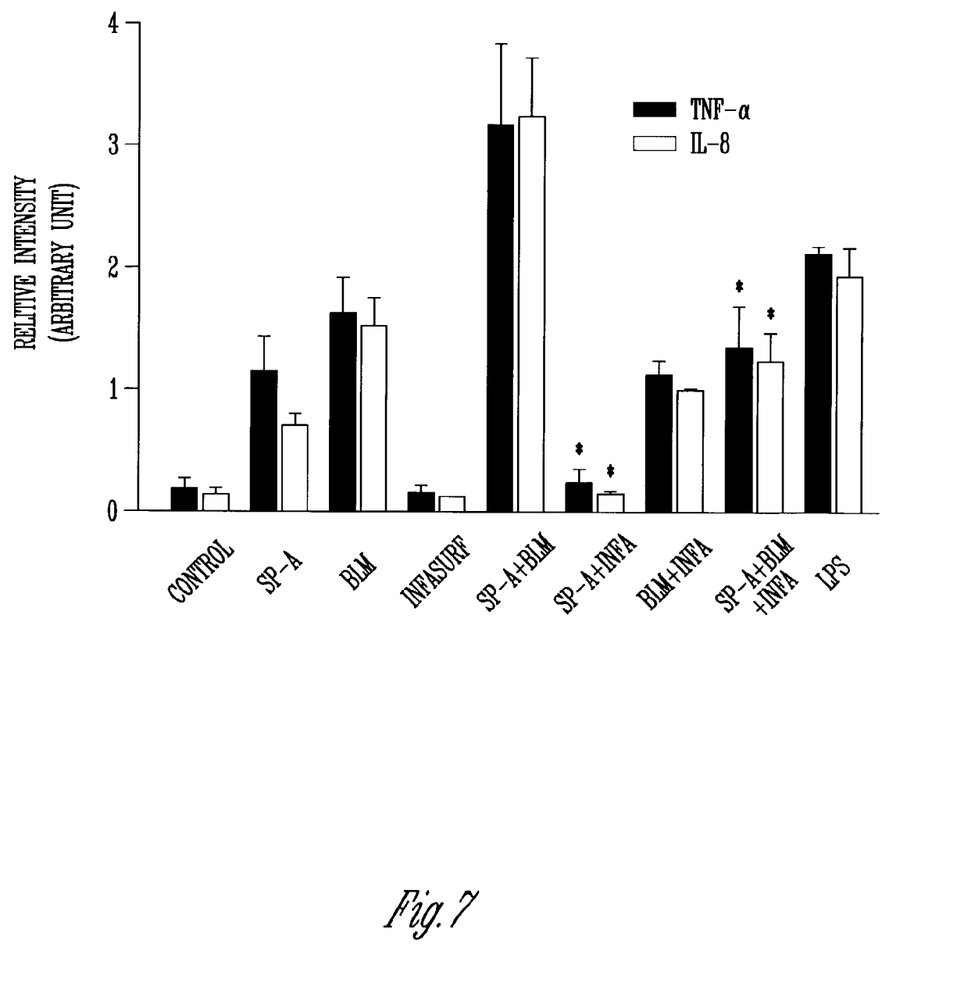
FIG. 7 illustrates the effect of surfactant lipids (Infasurf) on SP-A and bleomycin induced TNF-α, IL-8 mRNA expression. Infasurf (Infa; 400 μg/ml) was preincubated separately with SP-A (10 μg/ml), bleomycin (5 mU/ml), and SP-A+bleomycin 15 min at 37° C. before addition to THP-1 cells. Cells were incubated for 4 h after treatment. Cells were processed for quantification of cytokine mRNA by RPA. The mRNA levels of TNF-α and IL-8 in 2 μg of total RNA was normalized to the mRNA of the housekeeping gene GAPDH. Data shown are from 3 experiments. Results are given as means±SEM. The indicated values (*) are significantly different (p<0.05) from points obtained in the absence of Infasurf. BLM: bleomycin.

Similar results were obtained when TNF-α and IL-8 mRNA expression was measured by RPA (FIG. 7). TNF-α mRNA expression induced by SP-A was totally inhibited by Infasurf (400 μg/ml), but at the same time bleomycin-induced TNF-α mRNA level was not significantly changed. In SP-A+bleomycin treatment, the relative intensity of TNF-α mRNA was decreased from 3.17±0.71 in the absence of Infasurf to 1.14±0.10 in the presence of Infasurf. A similar response pattern was also seen for IL-8 mRNA after Infasurf treatment.

Discussion

The study demonstrates that SP-A plays a role in bleomycin-induced inflammation and that surfactant lipids modulate this process. With the macrophage-like THP-2 cell line, ribonuclease protection assay and ELISA were used and the following was observed: bleomycin (as has been shown for SP-A) enhances proinflammatory cytokine production by THP-1 cells. The combined bleomycin/SP-A on cytokine production is additive by ribonuclease protection assay and synergistic by ELISA. No effect on cytokine production is observed by Ara-C, a chemotherapeutic agent that has not been associated with lung inflammation and fibrosis, suggesting that the effect is specific to bleomycin and/or to agents or conditions associated with lung inflammation and fibrosis. The surfactant lipids significantly suppress the additive or synergistic effect on cytokine production observed in the presence of both SP-A and bleomycin. These data indicate that surfactant lipids may be useful in the suppression of inflammatory processes induced by SP-A and bleomycin or other inflammatory agents in the lung. This in turn should prevent lung fibrosis, a serious complication of chemotherapeutic agents such as bleomycin and other inflammatory agents.

Bleomycin stimulates THP-1 cells, a cell line of monocytic origin that upon vitamin $D_3$ differentiation acquires macrophage-like phenotype, to secrete cytokines in dose- and time-dependent patterns. The TNF-α time course observed is comparable to clinical observations about circulating TNF-α level after bleomycin treatment. Although some differences between the THP-1 cell line and alveolar macrophage were apparent in the kinetics and level of TNF-α and IL-1β induced by bleomycin treatment, the data presented demonstrates the usefulness of the THP-1 cell line as a model system for the study of bleomycin-induced cytokine production. Ara-C, another chemotherapeutic agent, can also cause pulmonary complications, but this is typically non-cardiogenic pulmonary edema rather than inflammation and fibrosis.

It has now been shown that SP-A in low dose (10 μg/ml) significantly increased cytokines at both the protein and mRNA levels. LPS (0.1 ng/ml) was used as a positive control. A striking difference in IL-1β mRNA expression between LPS and SP-A treated cells was observed, especially at 2 h after treatment (FIG. 3A). The relative intensity of IL-1β mRNA induced by LPS was 18-fold greater than that induced by SP-A (0.92±23 vs 0.05±0.02), while the differences between LPS and SP-A in TNF-α or IL-1β mRNA are only around 2-fold. These data may indicate that the regulation of proinflammatory cytokine production by SP-A in THP-1 cells occurs by a different pathway than that utilized by LPS.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence, which is effective to meet the objectives there intended, unless the context specifically indicates to the contrary.

All articles cited herein and in the following list are hereby expressly incorporated in their entirety by reference.

For the above-stated reasons, it is submitted that the present invention accomplishes at least all of its stated objectives.

What is claimed is:

1. A method of reducing pulmonary cytokine production caused by inflammatory agents and treating pulmonary fibrosis in animals comprising: administering to an animal between about 30–800 mg/kg of a composition comprising surfactant lipids; wherein the composition is administered by a method selected from the group consisting of intratracheally, orally, subcutaneously, intravenously, intranasally, rectally, sublingually, and buccally; and further providing that the surfactant lipids are administered concurrently with an agent selected from the group consisting of bleomycin, nitrofurantoin, amiodarone, cyclophosphamide, methotrexate, and mixtures thereof.

2. The method of claim 1 wherein the surfactant lipids are administered concurrently with bleomycin.

3. A composition for reducing pulmonary cytokine production caused by inflammatory agents and treating pulmonary fibrosis in animals, said composition comprising surfactant lipids and an agent selected from the group consisting of bleomycin, nitrofurantoin, amiodarone, cyclophosphamide, and methotrexate; and a pharmaceutically acceptable carrier.

4. The composition of claim 3 comprising 30–800 mg/kg surfactant lipids.

5. The composition of claim 3 whereby the agent is bleomycin.

6. A composition for reducing pulmonary cytokine production caused by inflammatory agents and treating pulmonary fibrosis in animals, said composition comprising surfactant lipids and an agent selected from the group consisting of bleomycin, nitrofurantoin, amiodarone, cyclophosphamide, methotrexate, and mixtures thereof; and a pharmaceutically acceptable carrier.

* * * * *

UNITED STATES PATENT AND TRADEMARK OFFICE
CERTIFICATE OF CORRECTION

PATENT NO.        : 6,998,384 B2
APPLICATION NO.   : 10/317787
DATED             : February 14, 2006
INVENTOR(S)       : Joanna Floros et al.

It is certified that error appears in the above-identified patent and that said Letters Patent is hereby corrected as shown below:

Col. 1, Line 10:

ADD
--GRANT REFERENCE
This invention was made with government support under Grant Nos. R01 ES09882 and R37 HL34788, awarded by the National Institutes of Health. The Government has certain rights in the invention.--

Signed and Sealed this

Twenty-second Day of June, 2010

David J. Kappos
*Director of the United States Patent and Trademark Office*